June 8, 1965 E. S. BOERNER Plant Pat. 2,530
ROSE PLANT
Filed Feb. 27, 1964
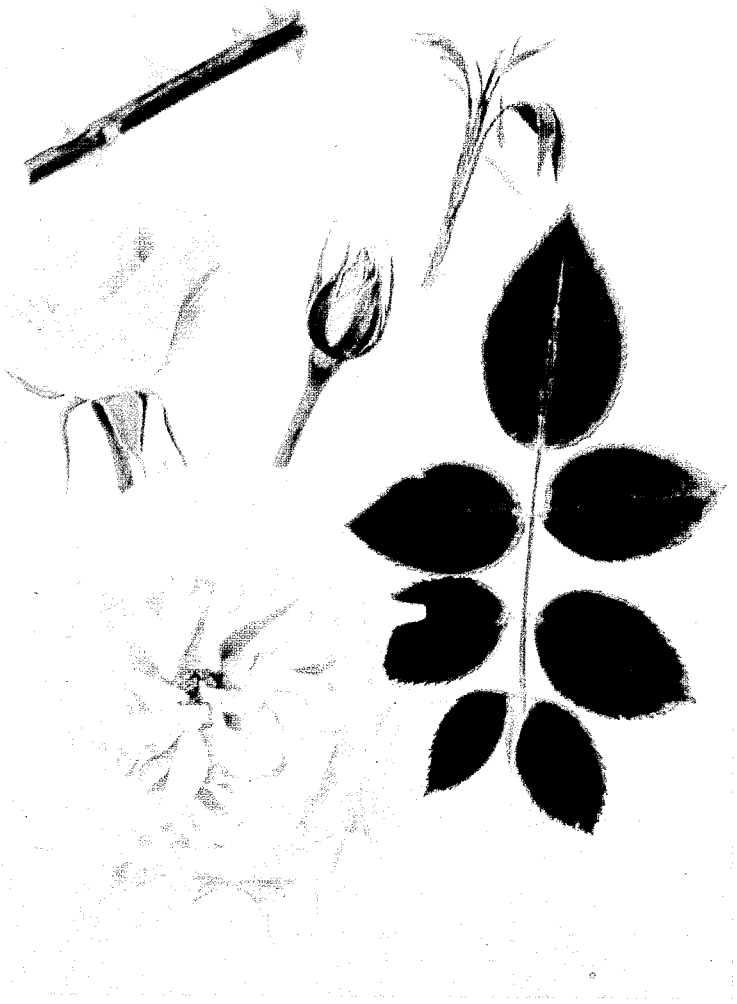
Inventor.
E. S. Boerner
By: Robb & Robb
Attorneys.

United States Patent Office

Plant Pat. 2,530
Patented June 8, 1965

2,530
ROSE PLANT

Eugene S. Boerner, Newark, N.Y., assignor to Jackson & Perkins Company, Newark, N.Y., a corporation of New York Filed Feb. 27, 1964, Ser. No. 347,984
1 Claim. (Cl. Plt.—11)

The present invention relates to a new and distinct variety of rose plant of the hybrid tea class, which was originated by me by crossing an unnamed and unpatented pink hybrid tea seedling of "Diamond Jubilee" (Plant Patent No. 824) with another well known variety named "Hawaii" (Plant Patent No. 1,833).

The primary objectives of this breeding were to produce a new hybrid tea rose variety which bears flowers that are long-lasting and retain their original color for a long time under both outdoor and indoor growing conditions, and also having a different color range and greater petalage than the flowers of the parent variety "Hawaii." These objectives were fully achieved, along with other desirable improvements, as evidenced by the following unique combination of characteristics which are outstanding in the new variety and which distinguish it from its parents, as well as from all other varieties of which I am aware:

(1) A very vigorous, upright and branching habit of growth which is different from either parent variety;

(2) A distinctive and attractive shape of the flowers in which the center petals are high when the flowers first open, and then gradually flatten to full petalled flowers;

(3) A distinctive and attractive general color tonality of the flowers corresponding to Eosine Pink, very lightly overcast with Rose Doree; and (4) Long-lasting qualities of the flowers and prolonged retention of the original flower color under both outdoor and indoor growing conditions.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed pink hybrid tea seedling of "Diamond Jubilee."
*Pollen parent.*—"Hawaii."

Classification:
*Botanic.*—Hybrid tea.
*Commercial.*—Hybrid tea.

*Flower*

(Observations made from specimens grown in a greenhouse at Newark, New York, in the early afternoon during the first half of the month of October.)

Blooming habit: Recurrent—continuous.

Bud:
*Size.*—Large.
*Form.*—Ovoid; is not affected by wet or hot weather.
*Color.*—When sepals first divide — Indian Lake, Plate 26. When petals begin to unfurl—Spinel Red, Plate 26, very lightly overcast with Indian Lake, Plate 26. When half-blown: inside of petals—Peach Red, Plate 1, very lightly overcast with Rose Doree, Plate 1; reverse of petals—Begonia Rose, Plate 1, with outer edges of petals Scarlet-Red, Plate 1.
*Sepals.*—Slightly branched: curl back when petals begin to unfurl. Color: inside—Light Fluorite Green, Plate 32; outside—Chromium Green, Plate 32.
*Calyx.* — Color — Chromium Green, Plate 32. Shape—pear. Size — small. Aspect — smooth. Odor when rubbed—none.
*Peduncle.*—Length — medium. Aspect — smooth. strength — erect; slender. Color — Light Bice Green, Plate 17.
*Opening.*—Opens up well; is not affected by adverse weather conditions.

Bloom:
*Size.*—Large. Average size when fully expanded—5 inches.
*Borne.*—Singly.
*Stems.*—Long; strong.
*Form (when first open).*—Center petals are high when blooms first open, and then blooms gradually flatten to full petalled flowers. Permanence — retains its form to the end.
*Petalage.*—Double (full but open center). Number of petals under normal conditions—from 60 to 65.
*Color.*—Center of flower—Begonia Rose, Plate 1, lightly overcast with Scarlet-Red, Plate 1. Outer petals—Tyrian Rose, Plate 12, very lightly overcast with Rose-Red, Plate 12. Base of petals (aiglet)—Pale Lemon Yellow, Plate 4. Inside of petals—Eosine Pink, Plate 1, very lightly overcast with Rose Doree, Plate 1. Reverse of petals — Begonia Rose, Plate 1, overcast lightly with Rose-Red, Plate 12.
*Discoloration.*—General tonality at end of first day—Eosine Pink, Plate 1, lightly overcast with Rose Doree, Plate 1. Second day—Eosine Pink, Plate 1, lightly overcast with Rose Doree, Plate 1. Third day—Eosine Pink, Plate 1, very lightly overcast with Rose Doree, Plate 1.

Petals:
*Texture.*—Leathery; is not affected by wet or hot weather.
*Appearance.* — Inside — satiny. Outside — shiny.
*Form.*—Oval.
*Arrangement.* — Imbricated (regularly arranged shingle-like).
*Petaloids in center.*—Few; large.
*Persistence.*—Drop off cleanly.
*Fragrance.* — Moderate. Nature — tea (average hybrid tea scent).
*Lasting quality.*—On the plant—very long. As cut flower—very long.

*Genital organs*

Stamens, anthers: Medium size; many; regularly arranged around styles. Color—Cadmium Orange, Plate 3.
Stamens, filaments (threads): Medium length. Color—Pinard Yellow, Plate 4.
Pollen: Color—Capucine Buff, Plate 3.
Styles: Columnar; uneven length; medium length; thin.
Stigmas: Color—Maize Yellow, Plate 4.
Ovaries: All enclosed in calyx.
Hips: None.
Seeds: None.

*Plant*

Form: Bush.
Growth: Very vigorous; upright; branching.
Foliage: Compound of 5–7 leaflets.
*Size.*—Large.
*Quantity.*—Abundant.

*Color.*—New foliage: upper side—Lettuce Green, Plate 5, very lightly overcast with Eugenia Red, Plate 13; under side—Oil Green, Plate 5, very lightly overcast with Acajou Red, Plate 13. Old foliage: upper side—Cerro Green, Plate 5; under side—Light Cress Green, Plate 31.

*Shape.*—Oval pointed.

*Texture.*—Upper side — leathery. Under side — smooth.

*Ribs and veins.*—Ordinary.

*Edge.*—Serrated (saw-toothed).

*Serration.*—Both double and single; small.

*Leaf stem.*—Color—Light Bice Green, Plate 17. Under side—Prickly.

*Stipules.*—Long; bearded.

Wood:

*New wood.*—Color—Cosse Green, Plate 5. Bark—smooth.

*Old wood.*—Color—Forest Green, Plate 17. Bark—smooth.

Thorns:

*Thorns.*—Quantity: on main stalks from base—ordinary; on laterals from stalk—ordinary. Form—flat base; medium length; some straight and some slightly hooked down. Color (when young) — Colonial Buff, Plate 30. Position—irregular.

*Prickles.*—Quantity: on main stalks — none; on laterals—none.

*Short needles.*—Quantity: on main stalks — none; on laterals—none.

I claim:

A new and distinct variety of rose plant of the hybrid tea class, substantially as herein shown and described, characterized particularly as to novelty by the unique combination of a very vigorous, upright, and branching habit of growth, a distinctive and attractive shape of the flowers evidenced by having high center petals when first opened and then gradually flattening to full petalled flowers, a distinctive and attractive general color tonality of the flowers corresponding to Eosine Pink, very lightly overcast with Rose Doree, and long-lasting qualities of the flowers and prolonged retention of the original flower color under both outdoor and indoor growing conditions.

No referenced cited.

ABRAHAM G. STONE, *Primary Examiner.*